US00PP18949P2

(12) United States Plant Patent
Bergman

(10) Patent No.: US PP18,949 P2
(45) Date of Patent: Jun. 17, 2008

(54) ***AZALEA* PLANT NAMED "YBAZ-2028 COTTON CANDY"**

(50) Latin Name: *Rhododendron hybrida*
Varietal Denomination: YBAZ-2028 Cotton Candy

(75) Inventor: Wendy R. Bergman, Lehigh Acres, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/725,801

(22) Filed: Mar. 20, 2007

(51) Int. Cl.
*A01H 5/00* (2006.01)

(52) U.S. Cl. ..... Plt./238

(58) Field of Classification Search ..... Plt./238
See application file for complete search history.

*Primary Examiner*—Annette H Para
(74) *Attorney, Agent, or Firm*—C. A. Whealy

(57) ABSTRACT

A new and distinct cultivar of *Azalea* plant named 'YBAZ-2028 Cotton Candy', characterized by its dark green-colored leaves that do not abscise during the cooling and forcing periods; uniform and outwardly spreading plant habit; freely branching habit; uniform and freely flowering habit; relatively rapid flowering response; large red purple-colored flowers; semi-double hose-in-hose flower form; and excellent postproduction longevity with plants maintaining good flower substance for about five weeks in an interior environment.

2 Drawing Sheets

Botanical designation: *Rhododendron hybrida.*
Cultivar denomination: 'YBAZ-2028 Cotton Candy'.

BACKGROUND OF THE INVENTION

The present Invention relates to a new and distinct cultivar of *Azalea*, botanically known as *Rhododendron hybrida,* an evergreen greenhouse-forcing type *Azalea*, and hereinafter referred to by the name 'YBAZ-2028 Cotton Candy'.

The new *Azalea* is a product of a planned breeding program conducted by the Inventor in Alva, Fla. The objective of the breeding program is to create new *Azalea* varieties having uniform plant habit, profuse and uniform flowering response, dark green foliage, good foliage retention during the cooling and forcing periods, resistance to Cylindrocladium and excellent postproduction longevity.

The new *Azalea* originated from a cross-pollination made by the Inventor in January, 1995, in Alva, Fla., of the *Azalea* cultivar Prize, disclosed in U.S. Plant Pat. No. 3,795, as the female, or seed, parent with a proprietary selection of Azalea identified as code number 93C-043-018, not patented, as the male, or pollen, parent. The new *Azalea* was discovered and selected by the Inventor as a flowering plant within the progeny of the stated cross-pollination in a controlled environment in Alva, Fla., on Dec. 27, 1999.

Asexual reproduction of the new *Azalea* by terminal cuttings taken in a controlled environment in Alva, Fla. since April, 2000, has shown that the unique features of this new *Azalea* are stable and reproduced true to type in successive generations.

SUMMARY OF THE INVENTION

The new *Azalea* has not been observed under all possible environmental conditions. The phenotype may vary somewhat with variations in environment such as temperature, daylength and/or light intensity without, however, any variance in genotype. The following traits have been repeatedly observed and are determined to be the unique characteristics of 'YBAZ-2028 Cotton Candy'. These characteristics in combination distinguish 'YBAZ-2028 Cotton Candy' as a new and distinct cultivar:

1. Dark green-colored leaves that do not abscise during the cooling and forcing periods.
2. Uniform and outwardly spreading plant habit.
3. Freely branching habit.
4. Uniform and freely flowering habit.
5. Relatively rapid flowering response; plants begin flowering about 25 days after cooling treatment.
6. Large red purple-colored flowers.
7. Semi-double hose-in-hose flower form.
8. Excellent postproduction longevity with plants maintaining good flower substance for about five weeks in an interior environment.

Plants of the new *Azalea* differ from plants of the female parent, the cultivar Prize, primarily in flower form and color as plants of the cultivar Prize have double hose-in-hose flowers that are darker in color than plants of the cultivar YBAZ-2028 Cotton Candy.

Plants of the new *Azalea* differ from plants of the male parent selection primarily in flower form and color as plants of the male parent selection have fully double flowers that are pale pink in color.

Plants of the new *Azalea* can be compared to the plants of the cultivar Party Favor, disclosed in U.S. Plant Pat. No. 10,050. In side-by-side comparisons conducted in Alva, Fla., plants of the new *Azalea* differed from plants of the cultivar Party Favor in the following characteristics:

1. Plants of the new *Azalea* had glossier foliage than plants of the cultivar Party Favor.
2. Plants of the new *Azalea* flowered earlier than plants of the cultivar Party Favor.
3. Flowers of plants of the new *Azalea* were not fragrant whereas flowers of plants of the cultivar Party Favor were slightly fragrant.

4. Plants of the new *Azalea* and the cultivar Party Favor differed in flower color as plants of the cultivar Party Favor had pink-colored flowers.

BRIEF DESCRIPTION OF THE PHOTOGRAPHS

The accompanying colored photographs illustrate the overall appearance of the new *Azalea*. These photographs show the colors as true as it is reasonably possible to obtain in colored reproductions of this type. Colors in the photographs may differ slightly from the color values cited in the detailed botanical description, which accurately describe the colors of the new *Azalea*.

The photograph on the first sheet comprises a side perspective view of a typical flowering plant of 'YBAZ-2028 Cotton Candy'.

The photograph on the second sheet is a close-up view of typical flowers of 'YBAZ-2028 Cotton Candy'.

DETAILED BOTANICAL DESCRIPTION

The aforementioned photographs and following observations and measurements describe plants grown in Alva, Fla. with three plants per 15-cm containers, in a polypropylene-covered shade house during the autumn and under commercial production conditions. During the production of the plants, day temperatures ranged from 13° C. to 37° C. and night temperatures ranged from 0° C. to 26° C. Plants were pinched at planting, pinched a second time about twelve weeks later, and then pinched a third time about twelve weeks after the second pinch. After sufficient flower bud development, plants were cooled at 3° C. to 5° C. for about four weeks to break flower bud dormancy. Plants were subsequently forced into flower under commercial production conditions in a polyethene-covered greenhouse. Plants used for the photographs and description were about one year old. In the following description, color references are made to The Royal Horticultural Society Colour Chart, 1995 Edition, except where general terms of ordinary dictionary significance are used.

Botanical classification: *Rhododendron hybrida,* 'YBAZ-2028 Cotton Candy'.

Commerical classification: Evergreen greenhouse-forcing type *Azalea.*

Parentage:

*Female, or seed, parent.*—*Rhododendron hybrida* cultivar Prize, disclosed in U.S. Plant Pat. No. 3,795.

*Male, or pollen, parent.*—Proprietary selection of *Rhododendron hybrida* identified as code number 93C-043-018, not patented.

Propagation:

*Type.*—By terminal vegetative cuttings.

*Time to initiate roots.*—Summer: About five weeks at temperatures of 24° C. Winter: About six weeks at temperatures of 24° C.

*Time to produce a rooted young plant.*—Summer: About nine weeks at temperatures of 24° C. Winter: About eleven weeks at temperatures of 24° C.

*Root description.*—Fine, fibrous, and white in color.

*Rooting habit.*—Freely branching; moderately dense.

Plant description:

*Plant form and growth habit.*—Perennial, evergreen; uniform and outwardly spreading plant habit; broad inverted triangle; moderately vigorous growth habit. Densely foliated; full and bushy plants. Uniform and freely flowering habit with numerous semi-double hose-in-hose flowers per plant.

*Branching habit.*—Freely branching; about six primary lateral branches develop after the initial pinch (removal of terminal apex); numerous secondary and tertiary branches develop after the sequential second and third pinches.

*Plant height, soil level to top of flowers.*—About 24 cm.

*Plant diameter, area of spread.*—About 44 cm.

*Lateral branch description.*—Length: About 18 cm. Diameter at base: About 4.5 mm. Internode length: About 1.1 cm. Strength: Strong. Texture, developing: Pubescent, fine brown hairs. Texture, mature: Woody; pubescent, fine brown hairs. Color, developing: Close to 144A. Color, mature: Close to 165A to 165B.

*Foliage description.*—Arrangement: Alternate, single. Foliage retention: Very good foliage retention on plants of the new *Azalea* that have been in a box for six weeks during the cooling treatment. Length: About 4.6 cm. Width: About 2.9 cm. Shape: Mostly obovate. Apex: Cuspidate to mucronate or obtuse. Base: Attenuate. Margin: Entire. Venation pattern: Pinnate. Texture, upper and lower surfaces: Glabrous or sparsely pubescent; leathery, tough. Color: Developing and fully expanded foliage, upper surface: Darker green than 147A; venation, close to 147A, towards the base, close to 146A. Developing and fully expanded foliage, lower surface: More green than 147B; venation, close to 146A to 146B. Petiole: Length: About 1 cm. Diameter: About 4 mm. Texture, upper and lower surfaces: Pubescent. Color, upper and lower surfaces: Close to 146B to 146C.

Flower description:

*Natural flowering season.*—Spring after sufficient cool period. If forced, plants typically flower about 25 days after a four-week cooling treatment; relatively rapid flowering response. Flowers persistent.

*Flower arrangement and appearance.*—Flowers arranged singly at terminals with usually about three flowers per apex; uniform and freely flowering habit. Flowers face upward or outward.

*Flower appearance.*—Flowers rotate and rose-like; semi-double hose-in-hose flower form with two whorls of petals.

*Postproduction longevity.*—Excellent postproduction longevity; under interior conditions, plants maintain good flower substance for about five weeks.

*Fragrance.*—None detected.

*Flower diameter.*—About 7.5 cm.

*Flower depth.*—About 3.25 cm.

*Flower bud (before showing color).*—Length: About 1.4 cm. Diameter: About 6 mm. Shape: Ovoid. Color: Close to 146B to 146C.

*Petals/petaloids.*—Arrangement: Semi-double hose-in-hose flower form; two whorls of petals each with about five imbricate petals and occasionally about five imbricate petaloids (transformed stamens); petals and petaloids fused at the base. Flowers appear full and rose-like. Petaloids variable in size and shape. Outer whorl of petals: Length: About 4 cm. Width: About 3.5 cm. Inner whorl of petals: Length: About 3.6 cm. Width: About 2.9 cm. Shape: Beyond fused base, roughly spatulate with rounded to bluntly acute apex. Margin: Entire; undulate; ruffled. Texture, upper and lower surfaces: Smooth, glabrous; velvety. Color: When opening and fully opened, upper surface: Close to 63A; towards the base, 63B to 63C; spots towards the base, close to 57A. When opening and fully opened, lower surface: Close to 63B; towards the base, 63B to 63C.

*Sepals.*—Arrangement: Five in a single whorl, fused; subtending the petals; petal-like; irregular in size and shape. Length: About 3.2 mm. Width: About 2.4 mm. Shape: Roughly spatulate. Apex: Rounded to acute. Base: Fused. Texture, upper surface: Smooth, velvety. Texture, lower surface: Pubescent. Color, upper surface: Close to 63A; towards the base, 63B to 63C; spots towards the base, close to 57A. Color, lower surface: Close to 63A to 63B; towards the base, 63B to 63C.

*Peduncles.*—Length: About 1.75 cm. Diameter: About 2 mm. Angle: Mostly upright. Strength: Flexible; strong. Texture: Very pubescent. Color: Close to 144A; towards the flower, tinted with 63A to 63B.

*Reproductive organs.*—Androecium: Occasionally transformed into petaloids. Quantity per flower: If not transformed, five. Filament length: About 2 cm. Filament color: Close to 155D. Anther length: About 3 mm. Anther shape: Oblong. Anther color: Close to 61A. Pollen amount: None observed. Gynoecium: Quantity of pistils per flower: Typically one. Pistil length: About 3.5 cm. Style length: About 3.3 cm. Style color: Close to 57A. Stigma shape: Rounded to flattened. Stigma diameter: About 1 mm. Stigma color: Close to 144A. Ovary color: Close to 146A; heavily whiskered.

*Seed/fruit.*—Seed and fruit development have not been observed.

Weather/temperature tolerance: Plants of the new *Azalea* have been observed to be very tolerant to rain and wind. Plants of the new *Azalea* have been observed to tolerate temperatures from about 0° C. to about 38° C.

Disease/pest resistance: Plants have not been observed to be resistant to pathogens and pests common to *Azaleas*.

It is claimed:

1. A new and distinct cultivar of *Azalea* plant named 'YBAZ-2028 Cotton Candy' as illustrated and described.

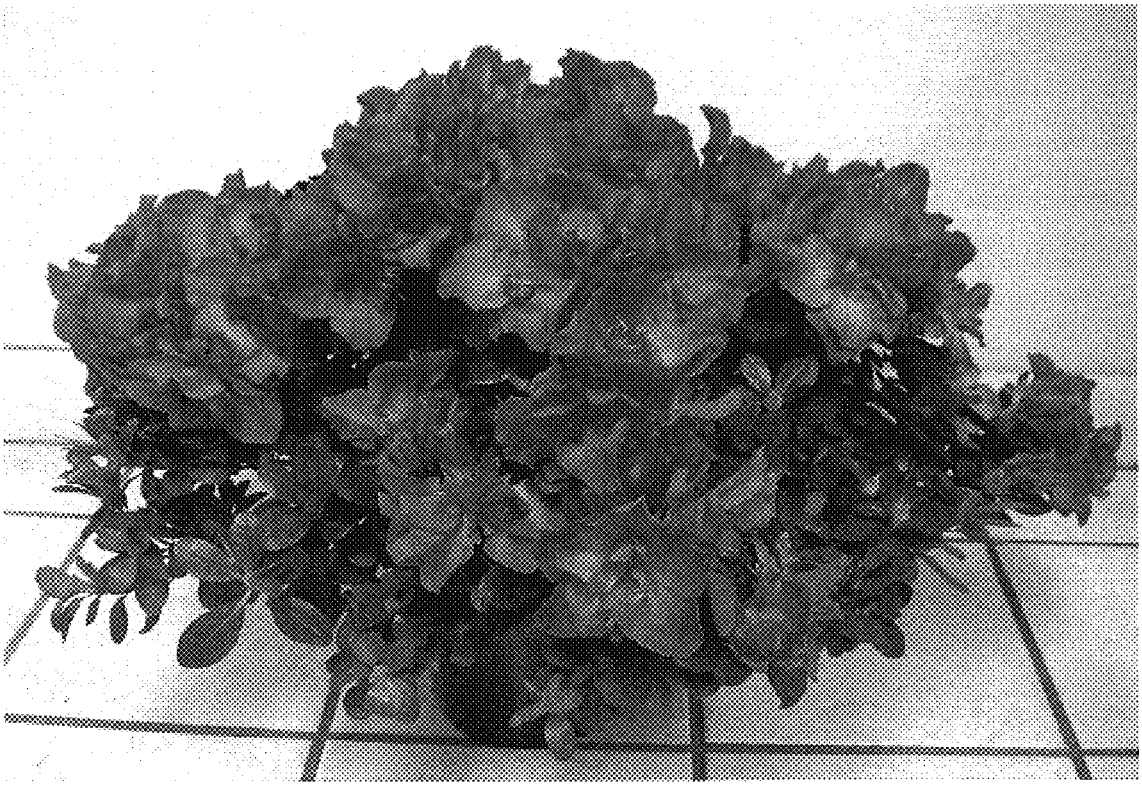

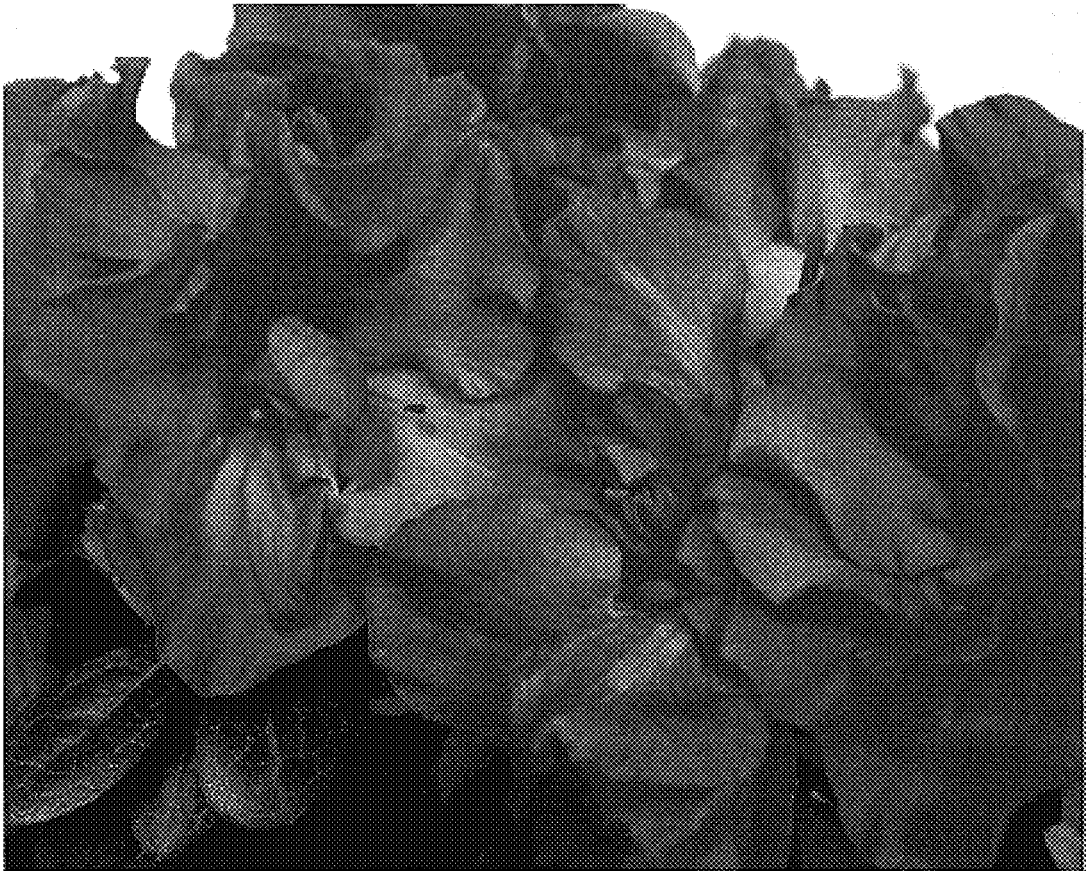

* * * * *